United States Patent [19]
Wilkinson

[11] Patent Number: 6,043,410
[45] Date of Patent: Mar. 28, 2000

[54] STRAWBERRY FRUIT PROMOTERS FOR GENE EXPRESSION

[75] Inventor: Jack Quinn Wilkinson, Davis, Calif.

[73] Assignee: Calgene LLC, Davis, Calif.

[21] Appl. No.: 09/020,033

[22] Filed: Feb. 6, 1998

[51] Int. Cl.[7] .......................... C12N 15/82; C12N 15/09; C12N 15/29; A01H 5/00; A01H 5/08

[52] U.S. Cl. ..................... 800/287; 435/69.1; 435/320.1; 435/419; 435/468; 536/23.6; 536/24.1; 536/24.5; 800/278; 800/279; 800/284; 800/286; 800/288; 800/298; 800/301

[58] Field of Search ............................... 435/69.1, 320.1, 435/410, 419, 468; 536/23.6, 24.1, 24.5; 800/278, 279, 284, 287, 288, 295, 298, 301, 286

[56] References Cited

FOREIGN PATENT DOCUMENTS

| | | | |
|---|---|---|---|
| WO 97/21816 | 6/1997 | United Kingdom | ............ C12N 15/29 |
| WO 97/27295 | 1/1997 | WIPO | ............ C12N 15/11 |
| WO 97 27308 | 7/1997 | WIPO . | |
| WO 98 31812 | 7/1998 | WIPO . | |

OTHER PUBLICATIONS

Kim et al, Plant Mol. Biol., vol. 24, pp. 105–117, 1994.
Stam et al, Annals of Botany, vol. 79, pp. 3–12, 1997.
Hain et al, Nature, vol. 361, pp. 153–156, 1993.
Wilkinson J Q et al., "Identification of mRNAs enhanced expression in ripening strawberry fruit using polymerase chain reaction differential display" Plant Molecular Biology, vol. 27, No. 6, Mar. 1, 1995 pp. 1097–1108.
Reddy A S N and Poovaiah B W: "Molecular cloning and sequencing of a cDNA for an auxin–repressed mRNA: correlation between fruit growth and repression of the auxin–regulated gene" Plant Molecular Biology, vol. 14, No. 2, Feb. 1990 (a990–02), pp. 127–136.

Reddy, et al., "Molecular cloning and sequencing of a cDNA for an auxin–repressed mRNA: correlation between fruit growth and repression of the auxin–regulated gene" *Plant Molecular Biology* 14:127–136 (1990).

Wilkinsin, et al., "Identification of mRNAs with enhanced expression in ripening strawberry fruit using polymerase chain reaction differential display" *Plant Molecular Biology* 27:1097–1108 (1995).

Manning, K., "Changes in gene expression during strawberry fruit ripening and their regulation by auxin" *Planta* 194:62–68 (1994).

Reddy, et al., "Molecular cloning of cDNAs for auxin–induced mRNAs and developmental expression of the auxin–inducible genes " *Plant Molecular Biology* 14:643–653 (1990).

*Primary Examiner*—David T. Fox
*Assistant Examiner*—Ashwin Mehta

[57] ABSTRACT

Promoters isolated from genomic DNA of strawberry plants are disclosed. The promoters are capable of tissue-specific expression in transgenic plants. A plant promoter that is a nucleic acid region located upstream of the 5' end of a plant DNA structural coding sequence that is transcribed at high levels in ripening fruit. This promoter region is capable of conferring high levels of transcription in ripening fruit tissue and in developing seed tissues when used as a promoter for a heterologous coding sequence in a chimeric gene. The promoter and any chimeric gene in which it may be used can be used to obtain transformed plants or plant cells. Chimeric genes including the isolated promoter region, transformed plants containing the isolated promoter regions, transformed plant cells and seeds are also disclosed.

10 Claims, 5 Drawing Sheets psar5 promoter  Length: 2061 bp  DS-DNA

```
   1 CTCGAGCACT AAACAAGTTA AGTAATCTCC CTATCTCTGT TACAAGCTTG TATTCTTTGG
  61 TTGTGTACTA ACCAATGTCA CTGTCATATT GATCCGGCTT AAGATGTTAC TGATGCTTAT
 121 GGGCGGTGAA GGTGGATATT CCAAAGGTAA GGTTGTTATA CAATACCGAA GAGTATACAT
 181 TCTATGCCTA AACTCCCAAT TTTTTTTTTT AATTTTTTGG TGACGAGAAA AACCATTGTG
 241 GTTCTTTCCT CCCATCATGT ATGGTGTCCT AATATTGGTG TTATTCACCT GGAAAAATTC
 301 GAACCAAGAA ACGTTTGAAC TAGCTGTGTT CTTGACTGGA GAGAATGAAT CAACTACGGA
 361 TTTTGAGAAA CAAATACTAT CCAACAAAGA AAATGAGGGA GAAATGTCCA TCTGCTAAAA
 421 TTGTTGGCGT GACCGCAACA GAGAGTCCAC GGCCCACTGA GAACCCTTGAC GGGCGAAGGC
 481 GCACTGCAAT ATCAGGGGTG GGGCCCATCT CAATGCATGC CACGACTACT ATATGTTAGT GCCCATATTT
 541 CTTTTTGATC CCACGGCCCA GTTCACTTAC CTTAGCTGGA AGTCAGTCTC ACGTTTATTA TTTGTTTTTA
 601 TTTCTTATAG GTTTAGCTCA CTTAGCTGGA ACTCAATATA CATGAAGCCC GAGCTACATA TAGGAATAAT
 661 AAAGTTTTGT ATCGGGAAAA ACTCAATATA CATGAAGCCC TCGACGATGG CTGCCCCGTCT ACTAGTTCT
 721 AAAAATCGGT CTGGGCGGCC GCCTAGACGC TCGACGATGG TTTCGATTGA CGATTCAAG
 781 CAAATCGTGT GGTCTGGGCG GCTGTCCGAT TTTCGATTGA TGGGCGGGTG TGGGCGGCGA
 841 TTACTCAGGC TAGGCGGCGA TTACTCGGGT TGGGCGGGTG GGCGGGTTGG CGGGACNAGA
 901 TTCTCTCAAC TGGAAATCGT CTTCGATATT GTCCACGTCC ATGAGAGATA GGAACCCTTG
 961 GAGCCTGAGT TGAAGACGAT AGAGAAGAAG ATGAAGGGAA CAGAATAAGG AGACGTGGGT
1021 TTTTAGTTCT TTATGATAAT TGAGATGAGT TATCTATTAC ATTAGGCTTA ATCTAATTGG
```

Fig. 1
1/2

```
1081 GTCTGGAAAG ATATTGACTT TACTGATGGG TATTCTTTTA ATAGCTTTTA CACAAATTAA
1141 TCCAATAATT GTTATCCGTT TTTCTAAGGA CAAGGTTTAG GATATAGTTT ATTAGGTGAT
1201 TAAAAATTAT TTAATATTAT ATTAAATGAT TATTTAAGTA AATAATTGCT TGTTATAATA
1261 ATTATATGCA TTATTTATAT AATTATCTAT TATTAAAAAT AAAATATTTA TACAAAAATA
1321 TAAATCCGAT TAATCCCCGA TTAAATCTTTT GGGCGCTATC CGCCCGACTA ACGCCTAACA
1381 TTTTTTAAAA CCTTGTACCT AAGAAAGCCT ATAACATCAT GAATCAATAT CATGCAAAAT
1441 CGTTTAAAGA AAACGTCTGA TTCCAACTCT GTCCATAGGA GTTGAATTCA GAATCCGGAG
1501 AATCTGAATT TAATTCTTTC TTTTATTATT TTCGTTCATT CTAAACGATG TTAAAAAAAT
1561 TTAGGACATG AGACTTAATA TCTAGAGCAG TGTCACACTT ATACCAAAGT AGGGAACCAA
1621 CGTGTCACTA TTAATCACAT GTCTCCCATC ATTCTGGGCC CTTCGTTGCTC TACGGAATAG
1681 GACAAGTATT CATATAGTAA GGGTACACTT GTGAACCAAG CCTCGTCTCA CTAAATTTCT
1741 CTATGAATTA TCTTTACATA GCGGGACCCC AGTTTACCAA GTCTTCATCC TTATCCATGT
1801 TTTCCTCCTT TTTCCACTCT CCAAATTATC CTACAACCAG TCGTAGAATT AGGAATTACC
1861 ACCCTGAGGT TGAAACTAAA GACACTTGGA AGTAGCAGAA CGGTGAAGAA CCCCATTATC
1921 AAATCAGTAA CTTTCTAATA GTAAACCCCA AGATATTTTT AGCTACCAAG CTCTCTTATA
1981 TATACAACCA TCCAGGAAAG ACCCAGAACA CACTAAAAAG GAAGAGATCG AGAAAGAAAG
2041 AAAGAGTTCA GAGCAAAGAT G
```

Fig. 1
2/2

RJ39C promoter Length: 874 bp DS-DNA

```
  1 TCTAGACTTG TATGCATTAC AGCACGAGCA GTTCATTTCA TGCATGACAT GAAAACAACG
 61 CGTGGTGCAA TCTACTAAAC CACGTGTACG GCTAATCTCA GGGGTTTTTC TAGGGTTTAG
121 AATGTTTCAA ACATCTATAT TAGGTTTTGG AGTTTGCATA GATACGTTCA AAAGTTAATA
181 GCAAATTTGA AGGTGTGCAA TGTTAACATT GACCTGTTAA CTTGTGATTT CTAGCTGTAA
241 AACAGATAAC GCTTTAGCTA ATGCTAAGTT TTCACATTTT CATTTTCGGG CTAAATATAT
301 GGTTGTGAGT AATGTTTCAG AGATACTTTT AACTTTTTGA AAGATATAGT CTCTTAATGG
361 ATATATATGA GATGTAATTT TATGAGTTAT CTGTTTCGAT TTGAATTCAC GTTTAGGTTT
421 AGGATTAGCT AGCACTTTAA CATTATCCTG AAATATCTTG GAAACAAATT TGGTGTTGTC
481 CTAACAATAA TATTATTGTG TTGAAATTTG CACATTGCAT TTTTATGTGT TGAAATTTTA
541 TCTAAAATGC TTGGTGGAGC ATAATAATTT GAAAAGAGAA AGAGTCAATA TGAATCCGAT
601 GCATTCTTGT CGTCCAGATT AACTATTTAA CAAATATCCA AATCTATCTA TATGGTTATA
661 AATTATATTT ATTTTCTAAA TTTACTTCCA TGTTTTTAAT TTGCCAGGTC ATCGATCTAA
721 TTACACGGTA GAGAATACTC ATGAAACTGG AATTCTGAAT ATTCACGTCA GCACAGATAT
781 TAGCTGGCTC TGCTTATCTT TCTCTCTATC CAACACTGTG ATTCAAACCC CCATTAAATC
841 CAGACCTACT GCCACACTGT CCCTTTCTTC CATG
```

STRAWBERRY FRUIT PROMOTERS FOR GENE EXPRESSION

TECHNICAL FIELD

The present invention relates to fruit tissue gene expression for the modification of fruit phenotype. The invention is exemplified by the use promoters from Fragaria sp. that express selectively in receptacle tissue.

BACKGROUND

One of the goals of plant genetic engineering is to obtain plants having improved characteristics or traits. Many different types of characteristics or traits in plants are considered advantageous. Those of particular importance with regard to fruit bearing plants include control of fruit ripening, improvements in the nutritional characteristics of the edible portions thereof, resistance to plant diseases, resistance to insects, cold tolerance and enhanced stability or shelf-life of the ultimate consumer product obtained from the plant.

At least two key components are required to stably engineer a desired trait, or control of such a trait, into a plant. The first key component comprises identifying and isolating the gene(s) which either encode(s) or regulate(s) a particular trait. The second component comprises identifying and isolating the genetic element(s) essential for the actual expression and/or selective control of the newly isolated gene(s) so that the plant will manifest the desired trait and, ideally, manifest the trait in a controlled or controllable manner. This second component, which controls or regulates gene expression, typically comprises transcriptional control elements known as promoters. Although a generic class of promoters which drive the expression of heterologous genes in plants have been identified, a broad variety of promoters active in specific target tissues or cells of plants remain to be described. The identification of such target or tissue-specific promoters is critical to the introduction of the above-mentioned tissue-specific improvements in plants such as fruit bearing plants.

Several promoters useful in expressing heterologous genes in selected fruits have already been identified. For example, the E4 and E8 promoters (Deikman, et al.), the kiwifruit actinidin promoter (Lin, et al.) and promoter for polygalacturonase are known to be fruit specific. U.S. Pat. No. 4,943,674 (Houck et al., Jul. 24, 1990) discloses a 2All promoter as useful in expression of a heterologous gene in tomato fruit. These promoters, however, have been isolated from fruit tissue which comprises mature or maturing ovaries (hereinafter referred to as "traditional fruit"). As such, these traditional fruit promoters would be ineffective in controlling desired traits in such accessory fruit bearing plants as strawberry, apple, pear, quince and the like wherein the major portion of the edible fruit comprises receptacle tissue (see *An Introduction to Plant Biology.* 2nd Edition, Braungart & Arnett, eds., C.V. Mosby Co. 1965). Similarly, to date, genes thought to be active in fruit tissue have been isolated from traditional fruit tissue instead of receptacle containing tissue. Promoters involved in fruit expression have been identified in PCT application WO 97/27295.

There exists a need for receptacle tissue selective promoters which provide for increasing or decreasing expression during fruit development, maturatioin and ripening in the art. Access to such receptacle tissue selective promoters would enable the genetic engineering of fruit tissue from commercially important plants such as strawberry, apple, and pear. Two cDNAs have been previously identified as receptacle tissue selective (Reddy and Poovaiah, 1990, Plant Molecular Biology, 14: 127–136 and Wilkinson et al., 1995, Plant Molecular Biology 27:1097–1108). The promoters for these two cDNAs were cloned and sequenced. Expression of reporter genes in strawberry plants will be used as an assay of the tissue specificity of the isolated promoters. Of particular interest are promoters which provide for recepticle tissue selective expression of genes. Also of interest is the ability to enhance or modify the properties of other promoters.

Relevant Literature

Reddy and Poovaiah, *Plant Mol. Biol.,* (1990) 14: 127–136, reports on the cloning of a cDNA for an auxin repressed mRNA from strawberry. Wilkinson, et al., *Plant Mol. Biol.,* (1995) 27:1097–1108 report the identification of mRNAs in strawberry with enhanced expression in ripening fruit, for example RJ39.

SUMMARY OF THE INVENTION

The present invention provides novel promoters, termed "SAR5 and RJ39", which cause decreasing or increasing tissue-selective expression of heterologous DNA in the receptacle tissue of plants.

The present invention also provides novel chimeric genes comprising a receptacle tissue-selective promoter operably coupled to a heterologous DNA sequence.

The present invention furthermore provides a method for expression of a heterologous gene, the improvement which comprises the use of an accessory fruit plant promoter which causes decreasing or increasing tissue-selective expression in seed, sink and receptacle tissue of plants during fruit development, maturation and ripening, said accessory fruit plant promoter having a sequence selected from the group consisting of those sequences shown in SEQ ID NOS. 1 and 2 and sequences substantially homologous thereto.

Novel transformed plant cells and transgenic plants comprising the heterologous genes of the present invention or produced by the methods of the present invention are additionally provided.

BRIEF DESCRIPTION OF THE DRAWINGS

FIG. 1(A–B) shows the nucleotide sequence (SEQ ID NO:1) of the full length promoter region of the SAR5 genomic DNA clone.

FIG. 2 shows the nucleotide sequence (SEQ ID NO:2) of the promoter region of the RJ39 genomic DNA clone.

FIG. 5 shows a schematic representation of the DNA vector, pCGN8052 containing the RJ39 promoter for plant transformation.

DETAILED DESCRIPTION OF THE PREFERRED EMBODIMENTS

Figure 3:
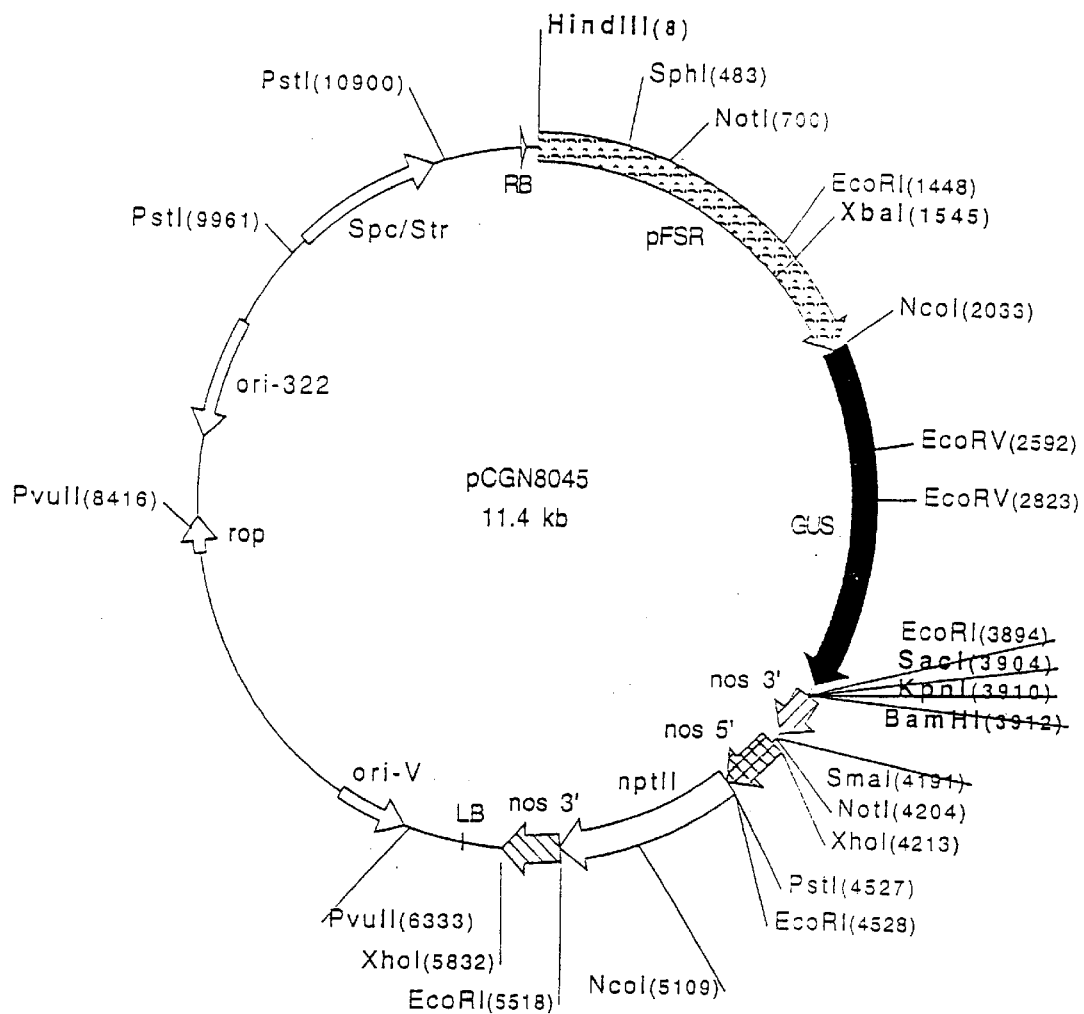
FIG. 3 shows a schematic representation of the primary DNA vector pCGN8045, containing the full length SAR5 promoter for plant transformation.
Figure 4:
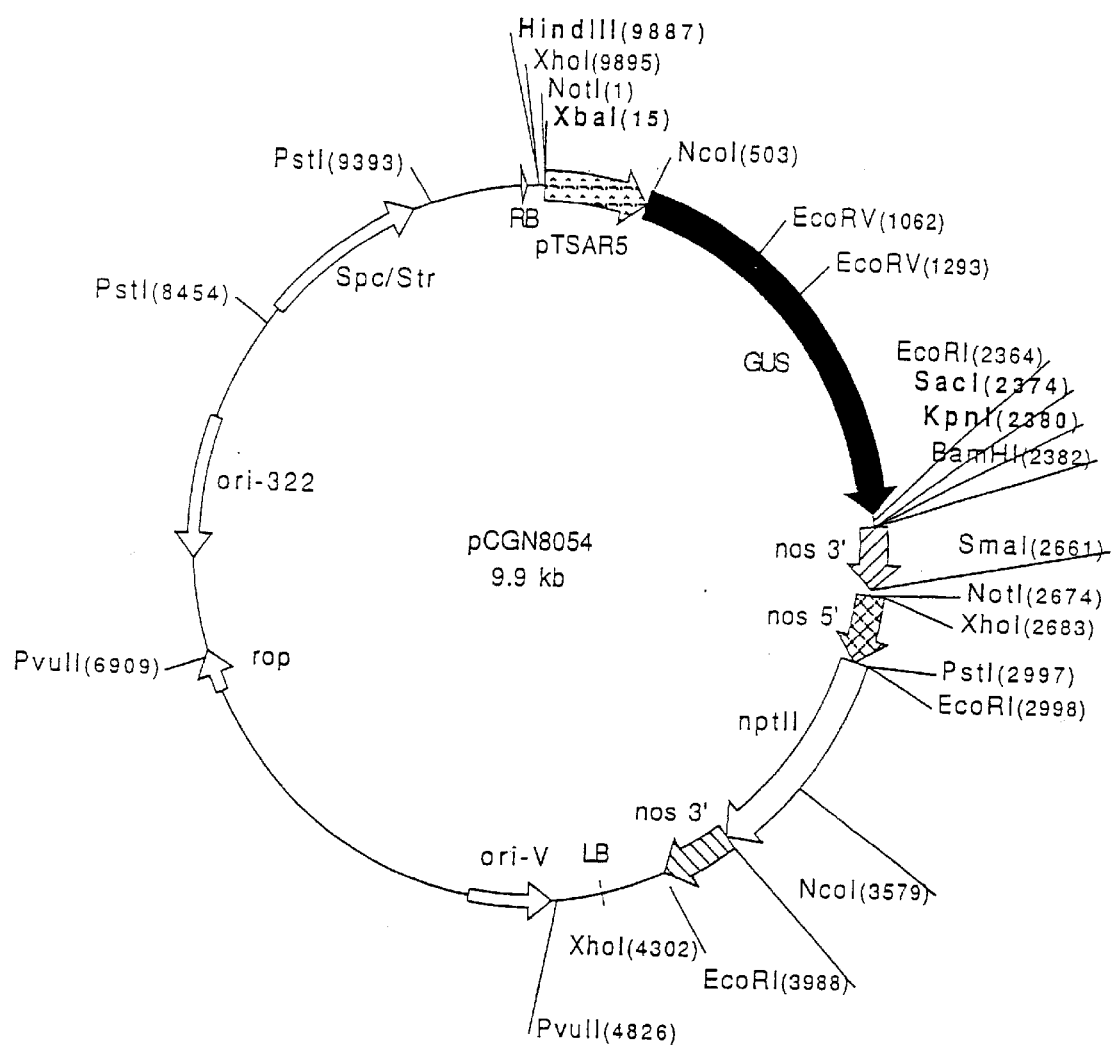
FIG. 4 shows a schematic representation of the DNA vector pCGN8054, containing the truncated SAR5 promoter for plant transformation.

In accordance with the subject invention, nucleic acid constructs are provided which are active in the receptacle tissue of plants, and in particular, accessory fruit bearing plants. The novel promoter sequences of the present invention provide for increasing or decreasing expression of heterologous genes during fruit development, maturation and ripening. The phrase "heterologous gene" means that the DNA coding sequence does not exist in nature in the same gene with the promoter to which it is now attached. The promoter sequences of the present invention now provide an opportunity to engineer agriculturally and commercially important traits into a class of fruits, fruit tissue and fruit bearing plants. More specifically, this class of fruits includes those plants comprising accessory fruit and other plants in which regulation of receptacle function or engineered expression in receptacle tissue is desirable. Constructs can be included in a transcriptional cassette or an expression cassette in which downstream from the regulated transcriptional initiation region is a nucleotide sequence of interest which provides for regulated modification of plant phenotype, by modulating the production of an endogenous product, as to amount, relative distribution, or the like, or production of an exogenous expression product to provide for a novel function or product. One or more introns also may be present. Depending upon the manner of introduction of the nucleic acid construct into a host plant, other DNA sequences may be required such as sufficient T-DNA from an Agrobacterium plasmid for transfer to a plant host. Plant hosts of particular interest are fruit plants, such as strawberry.

In one embodiment, DNA sequences for promoters are provided which are active in strawberry plants. Strawberry plants are an important commercial fruit crop in many temperate regions of the world and are especially suitable for improvement through genetic engineering techniques, such as clonal propagation, versus conventional breeding and selection. The high heterozygosity and polyploidy associated with commercial lines of strawberry plants hinder the improvement of such plants through traditional breeding methods. In contrast, clonal propagation of strawberry plants provides for stable transformation of a single dominant gene for a desired trait into a commercially important genotype without sexual recombination. The novel promoters of the present invention now provide an opportunity to engineer into such receptacle fruit bearing plants as strawberry such commercially and agriculturally desirable traits including delayed fruit ripening, increased sugar content, modified color and fungal resistance as more specifically described hereinafter.

In another embodiment of the present invention, receptacle tissue-selective promoter sequences are isolated from a genomic library created from Fragaria vesca DNA. Specifically, a probe is hybridized to *Fragaria vesca* genomic DNA fragments under medium to high stringency hybridization conditions (Maniatis et al., 1982). The identified genomic fragments are then isolated and purified. Confirmation of receptacle tissue-selective activity can then be achieved by transforming plants, or plant tissue with chimeric genes containing said substantially homologous sequences in accordance with the examples hereinafter.

In one important embodiment of the present invention, two distinct, novel promoters, each individually able to direct high level transcription of a second DNA sequence expressively coupled thereto in receptacle tissue of accessory fruit bearing plants, are provided. These promoters are designated SAR5 and RJ39 (also referred to as RJ39C). Nucleotide sequences of these promoters are provided in SEQ ID NOS. 1 and 2 respectively. It is understood by those of ordinary skill in the art that the DNA sequences shown in any of SEQ ID NOS. 1, and 2 include any promoter active in developing, maturing and ripening fruit receptacle tissue having a DNA sequence substantially homologous to any one of said promoter sequences. Strawberry fruit develops from receptacle tissue at the base of flowers. From the base of the flower, the receptacle tissue develops into ripened fruit receptacle tissue through the stages of: small green, large green, green-white, turning and full red stages.

Novel fruit selective promoters exhibiting decreasing or increasing and tissue selective expression during the development of the strawberry fruit have been isolated. An mRNA, RJ39, has been identified as having increased expression during fruit ripening, selectively in strawberry fruit receptacle tissue (Wilkinson et al., *Plant Mol. Biol.* (1995) 27:1097–1108). Expression of the RJ39 mRNA was observed at low levels in fruit in the green-white stage of fruit development. Expression of RJ39 increased during fruit ripening through the full-red stage of development.

The SAR5 mRNA is expressed during fruit development and maturation. SAR5 was identified as being repressed by auxin, and exhibited decreasing expression during strawberry fruit ripening (Reddy and Poovaiah, *Plant Mol. Biol.* (1990) 14:127–136). Expression initiated during flower bud development and increased during flower development and early fruit development, then decreased linearly during fruit maturation, and was expressed at very low levels or absent in turning and full red fruits.

These mRNAs expressed abundantly in the ripening receptacle tissue of accessory fruit plants (RJ39) or early in fruit development and maturation (SAR5) and showed little or no detectable expression in leaf tissues. The low number of hybridizing fragments, and the lack of sequence variability indicated a low gene copy number. The cDNA clones of RJ39 and SAR5 were used to isolate genomic clones which contained a genomic copy of the cDNA, and additional nucleic acid sequences corresponding to the transcriptional initiation region. Expression controlled by these promoters may be confirmed by fusion to the β-glucuronidase (GUS) gene and following the expression of the GUS enzyme during various stages of fruit development, maturation and ripening in transgenic fruit.

The promoters of the present invention may be used to increase the sugar content in fruit. In particular, one may inhibit the action of the plant glucose-6-phosphatase gene by controlling transcription of an antisense sequence corresponding to one or both of the subunits of glucose-6-phosphatase.

Other genes which might be usefully fused to a promoter of the present invention include sucrose phosphate synthase (SPS), which is thought to control the overall rate of sucrose biosynthesis in plant cells. Expression of an SPS gene, driven by SAR5 or RJ39 may result in a developing fruit with higher carbohydrate composition.

The use of promoters from the present invention with other genes such as ADP Glucose pyrophosphorylase, glgC16, encoding a starch synthesizing enzyme, may also be of interest. Expression of glgC16 driven by SAR5 or RJ39 may result in a developing fruit with higher carbohydrate composition.

Another possible use is with the invertase gene. Expression of invertase in a sink cell such as in a fruit is a method for increasing the ability of a cell to act as a stronger sink by breaking down sucrose to metabolites that can be used in carbon utilization pathways, e.g., starch biosynthesis. More sucrose is then mobilized into the sink tissue. Expression of invertase in the proper tissue and cellular compartments when the fruit is a strong sink, i.e., in a green fruit, is highly desirable.

The use of the promoters of the present invention with a gene for sucrose synthase would be desirable for the reasons given for SPS.

Other genes may be used in constructs with the SAR5 and RJ39 promoter sequences to achieve resistance to pathogens. For example, genes encoding for the production of phytoalexins (e.g. hydroxystilbenes), the expression of disease resistance genes, such as R genes, defense induction genes, such as avr genes, and genes for resistance to insects.

The promoters of the present invention may also be used in constructs containing two genes of complementary functions. For example, plants may be transformed with a construct containing two genes which may be complementary to each other to increase sugars in a fruit. One gene may be required in early fruit development, and the second gene product may act on the product of the early gene later in fruit ripening.

For example, the promoter SAR5 may be used to drive glgC16 early in fruit development to increase the amount of starch in developing fruit, and the RJ39 promoter may be used to drive SPS late in fruit development to further increase soluble solids in the fruit receptacle tissue.

Alternatively, the promoters may be used together to drive the same gene. By using the SAR5 and RJ39 promoters to drive the same gene, a sustained level of gene expression may be achieved during fruit development. For example, invertase may be driven by both SAR5 and RJ39 to provide for a constant, increased sink strength during fruit development and ripening.

Plants containing two or more promoter-gene fusions may be produced by several methods to one skilled in the art. A single construct containing two promoter-gene fusions may be used for transformation, or alternatively, two promoter-gene constructs may be used (cotransform). In addition, transgenic plants containing one of the promoter-gene fusions may be used as explant material to retransform with the second promoter-gene fusion. Transgenic plants containing two promoter-gene fusions may also be obtained by crossing transgenic plants containing one promoter-gene fusion integrated into it's genome.

By using the promoter sequences provided herein, one of ordinary skill in the art is now able to isolate, or chemically or enzymatically synthesize, by conventional methodologies, promoters having sequences essentially identical to those sequences described herein and promoters substantially homologous thereto. For example, the isolation of such promoter sequences can be achieved by using conventional techniques to synthesize a hybridization probe comprising all or a portion of a promoter sequence set forth in any of SEQ ID NOS. 1 and 2. The hybridization probe is preferably about 20 to 600 nucleotides in length.

A double-stranded DNA molecule containing one or more of the promoters of the present invention can be inserted into the genome of a plant by any suitable method. Suitable plant transformation vectors include those derived from a Ti plasmid of *Agrobacterium tumefaciens,* as well as those disclosed, e.g., by Herrera-Estrella, L., et al., Klee, H. J., et al., and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

A nucleotide sequence of interest is inserted downstream from and under the regulation of the transcriptional initiation region. The nucleotide sequence of interest provides for modification of plant phenotype for example by altering the production of an endogenous product, as to amount, relative distribution, or the like, or by encoding a structurally or functionally novel gene product. The nucleotide sequence may have any open reading frame encoding a peptide of interest, for example, an enzyme, or a sequence complementary to a genomic sequence, where the genomic sequence may be an open reading frame, an intron, a non-coding leader sequence, or any other sequence where the complementary sequence inhibits transcription, messenger RNA processing, e.g., splicing, or translation. The nucleotide sequence of interest may be synthetic, of natural origin, or combinations thereof. Depending upon the nature of the nucleotide sequence of interest, it may be desirable to synthesize the sequence with plant preferred codons. The plant preferred codons may be determined from the codons of highest frequency in the proteins expressed in the largest amount in the particular plant species of interest.

The termination region is one which is functional in a plant host cell. In addition to containing at least one terminating sequence, the termination region can include a poly A signal. In view of the relative interchangeability of the termination regions, the selection of a termination region for use in the expression construct is primarily based on convenience. The termination region and the transcriptional initiation region, or the termination region and nucleotide sequence of interest can originate from the same or different sources. Convenient termination regions are available from the Ti-plasmid of *A. tumefaciens,* such as the octopine synthase gene and nopaline synthase gene termination regions.

Additional DNA sequences can be included in the transcription cassette, for example, adapters or linkers for joining the DNA fragments in the proper orientation and, as appropriate, in the proper reading frame. Other DNA sequences may be needed to transfer transcription constructs into organisms used for transforming plant cells, e.g., *A. tumefaciens.* In this regard, the use of T-DNA of the Ti- or Ri- plasmids as a flanking region in a transcription construct is described in EPO Application No. 116,718 and PCT Application Nos. WO84/02913, 02919 and 02920. See also Herrera-Estrella, *Nature* (1983) 303:209–213; Fraley et al., *Proc. Natl. Acad. Sci,* USA (1983) 80:4803–4807; Horsch et al., *Science* (1984) 223:496–498; and DeBlock et al., *EMBO J.* (1984) 3:1681–1689.

The expression constructs of the present invention, which contain the regulated 5'-untranslated regions of two receptacle selective genes from strawberry, are transformed into plant cells to evaluate their ability to function with a structural gene other than the open reading frame that is natively associated with the 5'-untranslated region and to ascertain their expression characteristics.

A variety of techniques are available for the introduction of DNA into a plant cell host. These techniques include transformation employing Ti-plasmid DNA and *A. tumefaciens* or *A. rhizogenes* as the transforming agent, protoplast fusion, injection, electroporation, and the like. The transcription construct normally is joined to a marker that allows for selection of transformed cells in the treated population, for example, resistance to antibiotics such as kanamycin, G418, bleomycin, chloramphenicol and others.

Any plant variety may be employed as a host cell in accordance with this invention. Of particular interest are agricultural fruit crops, such as strawberries and tomatoes, although the use of the RJ39 and SAR5 transcriptional initiation regions in other plants, including other fruit-bearing plants is also considered. Examples of plants in which the promoters of the present invention may find use include, but are not limited to, any sink tissue of plants including strawberry, raspberry, tomato, potato tuber, tobacco, soybean, cotton boll, and cotton seed.

The transformed plant host cells are used to regenerate plants. See, e.g., McCormick et al., *Plant Cell Reports* (1986) 5: 81–84. These plants are then grown and pollinated with either the same transformed strain or with different strains, and the resulting hybrid having the desired phenotypic characteristic identified. Two or more generations may be grown to ensure that the desired phenotypic characteristic is stable maintained and inherited and then seeds harvested to ensure the desired phenotype or other property has been achieved.

The embodiments described above and the following examples are provided to better elucidate the practice of the present invention. It should be understood that these embodiments and examples are provided for illustrative purposes only, and are not by way of limitation of the scope of the invention.

The following experimental protocol describes the identification and isolation of the promoter of a gene differentially expressed in the receptacle tissue of plants. One skilled in the art will recognize that substitutions and alterations may be made in the components, conditions, and procedures presented herein without departing from the scope or intention of the protocol. The recombinant DNA techniques employed are familiar to those skilled in the art of manipulating and cloning DNA fragments and employed persuant to the teachings of Sambrook et al.

EXAMPLES

Example 1

Isolation of Promoters

A. Isolation of Strawberry Genomic DNA

Strawberry genomic DNA was isolated from *Fragaria vesca* (2n=14) and Fragaria x ananassa (variety Redcoat) as described here. Fresh or frozen strawberry leaf tissue was ground in a chilled mortar and pestle, and 2 volumes (v/w of fresh tissue) of DNA Extraction Buffer (500 mM Sorbitol, 100 mM Tris, 5 mM EDTA, 2% β-mercaptoethanol, pH 7.5) was added, and ground again briefly. Homogenate was transfered to a centrifuge tube and 2.5 volumes of Nuclei Lysis Buffer (200 mM Tris, 50 mM EDTA, 2M NaCl, and 2% CTAB (hexadecyltrimethylammonium bromide), pH 7.5) was added with 0.5 volumes 5% Sarkosyl solution. Homogenates were mixed briefly by inversion, then incubated at 65° C. for 15 minutes. DNA solutions were mixed again at room temperature for 5 minutes by inversion. Samples were chloroform extracted one time with an equal volume of chloroform/ isoamyl alcohol (24:1). The samples were centrifuged at 12,000 rpm for 15 minutes, and the top, aqueous phase was transfered to a new tube. The genomic DNA was precipitated by adding one volume of isopropanol, incubated for 30 minutes on ice and centrifuged for 10 minutes at 12,000×g. DNA pellets were washed with 70% ethanol, and air dried. Two additional steps were used to remove contaminating polysaccharides. Dried pellets were resuspended in TE, and ¼ volume 5M NaCl was added. Samples were then incubated on ice for 30 minutes, and centrifuged for 10 minutes at 12,000×g. The supernatant was transferred to a new tube and the DNA precipitated with 2.5 volumes of ethanol. The dried pellets were resuspended in TE. Potassium acetate (2M final concentration) was added, and samples were incubated again on ice for 30 minutes and centrifuged for 10 minutes at 12,000×g. DNA in the supernatant was precipitated, dried, and resuspended in TE.

B. Isolation of SAR5 Promoter

A genomic clone of the SAR5 gene was obtained by PCR amplification of strawberry genomic DNA using the primers designed according to the sequence of SAR5 (Reddy and Poovaiah, 1990, Plant Molecular Biology, 14:127–136). The forward PCR primer SAR5-5C1 (5'-TCGAATTCAGAGCAAAG<u>ATG</u>GTTCTGC-3', SEQ ID NO:3) contains SAR5 encoding sequence from the 5' end of the cDNA, including the ATG start codon (underlined above) and restriction cloning sites. SAR5-3N2 (5'-ACCTCGAGGGATCCTCATCACTTGTCG-3', SEQ ID NO:4) is the reverse primer containing complementary sequences to bases 369 to 386 in the 3'-untranslated region (numbering according to Reddy and Poovaiah) and restriction cloning sites. The genomic DNA was prepared from strawberry (variety Redcoat) leaf tissue using the method described in 1A above. PCR amplification was carried out according to the manufacturer's recommendations (Perkin-Elmer) at 40 cycles of 94 degrees C. 1 min., 49 degrees C. 1 min., and 72 degrees C. 1 min. The PCR product was purified from an agarose gel slice using a Prep-A-Gene kit (BioRad), digested with EcoRI and BamHI, and cloned into the EcoRI and BamHI sites of pBluescript SK- (Stratagene) creating the clone pCGN8023. Analysis of sequence obtained using an ABI automated sequencer demonstrated that a complete genomic DNA copy of SAR5 was obtained and contained two introns.

In order to reduce some of the complexities involved in cloning from an octoploid species, such as Fragaria x ananassa (variety Redcoat, 8n=56), DNA from a diploid species, *Fragaria vesca* was used to clone the SAR5 promoter. Strawberry genomic DNA was prepared from Fragaria vesca as described in example 1A above. DNA was digested with the restriction enzyme BglII and the digestion products were separated on a 0.7% agarose gel. The digested, fractionated DNA fragments were transferred to a positively charged nylon membrane (Nytran) by capillary blotting overnight in 10× SSC buffer (Southern transfer). A radioactive probe was prepared from the first 450 bp of the SAR5 genomic clone (up to the BglII site) using a Prime-It kit (Stratagene) and the filter was incubated overnight in hybridization solution at 60 degrees C. The filter was subsequently washed to eliminate non-specific probe binding, with the final wash being 0.25× SSC, 0.1% SDS at 60 degrees C. The results after X-ray film exposure indicated that SAR5 is a single-copy gene in *F. vesca*.

*F. vesca* genomic DNA was digested with BglII in combination with EcoRI, PstI, XhoI, or SpeI, followed by Southern blotting and hybridization as described above. From the size of the hybridizing bands in each lane, a restriction map of the SAR5 promoter region (extending down to the internal BglII site) was generated. The restriction map indicated that a promoter fragment of approximately 6 kb (PstI), 3.6 kb (SpeI), 2 kb (XhoI), or 0.5 kb (EcoRI) could be obtained by cutting with the appropriate enzyme in combination with BglII.

*F. vesca* genomic DNA was cut with XhoI and BglII, fractionated on a 0.7% agarose gel, and the gel region around 2.5 kb (2kb promoter+450 bp coding region) excised with a razor blade. DNA from the gel piece was purified using a Prep-A-Gene kit and ligated to XhoI- and BamHI-digested pBluescript SK- DNA. The ligation mix was transformed into competent *E.coli* cells which were then plated out onto selection media. Ampicillin-resistant colonies were patched in a grid format to new plates and then lysed onto nitrocellulose filters for in situ hybridization (Sanmbrook et al. Molecular Cloning).

A probe corresponding to the first 450 bp of the SAR5 genomic clone was prepared using an ECL Labeling and Detection kit and used to screen the filters according to the manufacturer's instructions (Amersham). After X-ray film exposure, one positive colony was identified. This colony was inoculated into liquid media for overnight growth and plasmid DNA was prepared using a Qiaprep Spin Miniprep kit (Qiagen). The plasmid DNA was analyzed by restriction enzyme analysis and then sequenced using an ABI automated sequencer. The clone was verified as containing 5' flanking sequence (the SAR5 promoter) and a portion of the SAR5 coding region (up to the internal BglII site). The clone was designated pGSAR5-16

A BamHI restriction site was introduced upstream of the SAR5 initiation codon (ATG) by PCR amplification of the above promoter clone with the primers pSAR5-BH1 (5'-TAGGATCCGTCTTTGCTCTGAACTC-3', SEQ ID NO:5) and pSAR5-R4 (5'-ACCTTGTACCTAAGAAAGCC-3', SEQ ID NO:6). The PCR product was purified from an agarose gel slice using a Prep-A-Gene kit, digested with XbaI and BamHI, and cloned into the XbaI and BamHI sites of pBluescript SK-, yielding the plasmid pSAR5PCR/pSK- (also referred to as the truncated or TSAR5 promoter,).

To facilitate other cloning experiments, the TSAR5 promoter was subcloned as an XbaI to EcoRI fragment into the XbaI to EcoRI sites of pUC119, creating the plasmid pCGN8046. The full-length SAR5 promoter, referred to as FSR or pCGN8047 (SEQ ID NO:1), was recreated by cloning the upstream region from the original promoter clone as an XhoI to XbaI fragment into the SalI to XbaI sites pCGN8046. Plasmids containing the reconstructed full-length promoter with a BamHI site introduced just upstream of the SAR5 initation codon were identified by restriction enzyme analysis.

B. Isolation of RJ39 Promoter

The strawberry ripening-induced cDNA clone RJ39 was originally isolated by Wilkinson, Lanahan, Conner, and Klee (Plant Molecular Biology 27:1097–1108, 1995) using a polymerase chain reaction differential display technique to compare mRNA populations from white vs. full-red berries. Northern analyses revealed that the RJ39 mRNA is strongly fruit-enhanced or fruit-specific, with expression levels increasing as the fruit develop from the small green to full-red stage. Little or no expression was detected in leaf, petiole, or root tissues. The cDNA clone that was isolated was not full-length (571 bp vs. roughly 850 bp transcript on Northern blots), and the translation product of this cDNA showed no significant homology to any known proteins.

A genomic clone containing the RJ39 coding region and 5' flanking sequences (promoter) was obtained in a manner similar to that described for the SAR5 promoter. Strawberry genomic DNA was prepared from Fragaria vesca (2n=14) as described in Example 1A. An aliquot of DNA was digested with the restriction enzyme XbaI and then the DNA fragments were separated on a 0.7% agarose gel. The digested, fractionated DNA fragments were transferred to a positively charged nylon membrane (Nytran) by capillary blotting overnight in 10× SSC buffer (Southern transfer). A radioactive probe was prepared from the first 400 bp of the RJ39 cDNA clone (up to the XbaI site) using a Prime-It kit (Stratagene) and the filter was incubated overnight in hybridization solution at 60 degrees C. The filter was subsequently washed to eliminate non-specific probe binding, with the final wash being 0.25× SSC, 0.1% SDS at 60 degrees C. The results after X-ray film exposure indicated that RJ39 is a single-copy gene in F. vesca.

Aliquots of F. vesca genomic DNA were digested with XbaI in combination with EcoRI, PstI, XhoI, SpeI, BglII, HindIII, EcoRV, SphI, or SalI, followed by Southern blotting and hybridization as described above. From the size of the hybridizing bands in each lane, it was determined that the only restriction site inside of the 5' flanking XbaI site was EcoRI (band of approximately 1.1 kb). All other restriction enzymes tested gave the same size band (approximately 1.9 kb) as F. vesca genomic DNA cut with XbaI alone. In order to obtain a functional promoter fragment, a genomic clone of approximately 1.8–2 kb, which contains the entire RJ39 coding region and roughly 900 bp of promoter sequence, should be obtained.

F. vesca genomic DNA was cut with XbaI, fractionated on a 0.7% agarose gel, and the gel region between 1.6–2 kb excised with a razor blade. DNA from the gel piece was purified using a Prep-A-Gene kit and ligated to SpeI-digested, alkaline phosphatase-treated pBluescript SK- DNA. The ligation mix was transformed into competent E.coli cells which were then plated out onto selection media containing IPTG and X-GAL. White, ampicillin-resistant colonies were patched in a grid format to new plates and then lysed onto nitrocellulose filters for in situ hybridization (Sambrook et al., Molecular Cloning)

A probe corresponding to the first 400 bp of the RJ39 cDNA clone was prepared using a Prime-It kit (Stratagene) and used to screen the filters in a manner similar to that used for the Southern blots. The hybridization temperature was 65 degrees C. and the final wash was 0.15× SSC, 0.1% SDS at 65 degrees C. After X-ray film exposure, several positive colonies were identified. These colonies were inoculated into liquid media for overnight growth and plasmid DNA was prepared using a Qiaprep Spin Miniprep kit (Qiagen). The plasmid DNA was analyzed by restriction enzyme analysis and 2 clones were selected. Sequence analysis of the two clones demonstrated that both clones contained 5' flanking sequence (the RJ39 promoter) and the complete RJ39 coding region (down to the XbaI site in the 3' flanking sequence). One clone, designated pRJ39C#N-91, was selected for further cloning.

A BglII restriction site was introduced upstream of the RJ39 initiation codon (ATG) by PCR amplification (with Pfu polymerase) of pRJ39C#N-91 with the primers RJ39C-3N1 (5'-AACTGCAGATCTAGTGTGGCAGTAGGTCTG-3', SEQ ID NO:7) and T7 promoter primer (5'-TAATACGACTCACTATAGGG-3', SEQ ID NO:8). The PCR product was purified from an agarose gel slice using a Prep-A-Gene kit, digested with BamHI, and ligated to SmaI- and BamHI-digested pUC119 creating the plasmid pCGN8051.

Example 2

Preparation of Plant Expression Constructs

The expression construct pCGN8014 was used as a cloning vector for plant transformation. The vector is a derivative of the vector pMON18354 which is described in provisional U.S. patent application Ser. No. 60/036,131, and regular application claiming priority, therein application number 09/008,979 filed Jan. 20, 1998, which disclosure is incorporated herein by reference. The pMON18354 was modified by transposing the fragment containing the nopaline synthase (nos 5') promoter, neomycin phosphotransferase (nptII) kanamycin resistance gene, and nos termination (nos 3') sequences from between the right border and SRE49 promoter to the 3' postion between the β-glucoronidase (GUS) reporter gene, nos 3' elements and the left border sequence. The modification yielded the vector pCGN8014.

Another binary vector for plant transformation, pCGN5928, was constructed using the neomycin phosphotransferase (nptII) kanamycin resistance gene driven by the nopaline synthase transcriptional initiation region (nos 5') and transcription termination (nos 3') sequences (Fraley et al., *Proc. Natl. Acad. Sci* (1983) 80:4803–4807 and Depicker et al., *J. Molec. Appl. Genet.* (1982) 1: 562–573). Both the nos 5' and nos 3' were PCR amplified from the *Agrobacterium tumafaciens* strain C58 and linked together with the nptII gene from pCGN783 (Houck, et al., *Frontiers Appl Microbiol* (1988)4) as an EcoR I fragment to form pCGN5908. The nos 5'-nptII-nos3' fragment was then cloned into pCGN1541, containing ori322, Right border (0.5 Kb), lacZ, Left Border (0.58 Kb), as an Xho I fragment between the Right border-lacz and Left border sequences to create the intermediate pCGN5910. The ColEI and pRi origins of replication as well as the Gentamycin resistance gene were aquired from a Not I deleted derivative of pCGN1532 (McBride and Summerfelt, *Plant Molecular Biology*, (1990), 14:269–276) as a BamH I fragment to create pCGN5924. Finally, a linker containing unique restriction sites was synthesized and cloned into the Asp 718/Hind III (within the lacZ sequence) sites of pCGN5924 to create the binary vector pCGN5928.

Plant transformation vectors were constructed to test the strength and tissue specificity of TSAR5 and FSR promoters in transgenic plants using the GUS reporter gene as a marker. Vector pCGN8045 was created by cloning the FSR promoter from pCGN8047 as a HindIII to BamHI fragment into the HindIII to BglII sites of pCGN8014. The order of genetic elements in the T-DNA are: RB-pFSR-GUS-nos3'-nos5'-nptII-nos3'-LB. Vector pCGN8054 was created by cloning the TSAR5 promoter piece from pCGN8046 as an XbaI to BamHI fragment into the XbaI to BglII sites of pCGN8014. The order of genetic elements in the T-DNA are: RB-pTSAR5-GUS-nos3'-nos5'-nptII-nos3'-LB. These vectors were transformed into an appropriate Agrobacterium strain and can be used to generate transgenic strawberry plants for evaluation of the promoters.

A binary vector was constructed to test the strength and tissue specificity of the RJ39 promoter in transgenic plants using the beta-glucuronidase (GUS) reporter gene as a marker. Vector pCGN8052 was created by cloning the RJ39 promoter from pCGN8051 as an XbaI to BglII fragment into the XbaI to BglII sites of pCGN8014. The order of genetic elements in the T-DNA are: RB-pRJ39C-GUS-nos3'-nos5'-nptII-nos3'-LB. (The RJ39 promoter has also been referred to as RJ39C). This vector was transformed into an appropriate Agrobacterium strain and can be used to generate transgenic strawberry plants for evaluation of the promoter.

Two additional DNA fusion constructs were prepared, one containing the full length SAR5 promoter controlling glgC16, and one containing the truncated SAR5 promoter controlling glgC16. The constructs were prepared as follows.

The plant transformation vector pCGN8040 contains glgC16 under the control of the truncated SAR5 promoter. The truncated SAR5 promoter (TSAR5) was cloned as a PstI-BamHI fragment into the PstI and BglII sites of pCGN8222 creating the plasmid pCGN8039. The TSAR5 promoter replaces the TFM7 promoter in pCGN8222. PCGN8222 was created by cloning the glgC16 encoding sequence from pMON18345 (described in U.S. Pat. No. 5,608,150) as a BglII-SacI fragment into pMON18337 (described in provisional U.S. patent application Ser. No. 60/036,131 and regular application claiming priority, therein application number 09/008,979 filed Jan. 20, 1998). The TSAR5-glgC16-nos 3' fragment was cloned from pCGN8039 as a PstI-NotI fragment into the binary vector pCGN5928, SseI-NotI sites, to create the plant expression vector pCGN8040.

The plant transformation vector pCGN8042 also contains glgC16, but is under the control of the full length SAR5 promoter. The full length SAR5 promoter (FSR) was cloned from pCGN8047 as a PstI-BamHI fragment into pCGN8222, PstI-BglII sites, to form the plasmid pCGN8041. The fSAR5-glgC16-nos 3' fragment was cloned as a PstI-NotI fragment into the SseI-NotI restriction sites of pCGN5928 yielding the plant expression vector pCGN8042.

Plant transformation vectors were transformed into Agrobacterium tumefaciens strain LBA4404 by the method of Holsters et al., Molecular and General Genetics (1979) 163:181–187.

Example 3

Plant Transformation

Transgenic strawberry plants may be obtained using the methods of Nehra, N. S. et al. (*Plant Cell Rep.* (1990) 9:10–13 and *Plant Cell Rep.* (1990), 9:293–298), Matthews, H. V. et al., (*In Vitro Cell. Dev. Biol.* (1995) 31:36–43 and WO 95/35388, Dec. 28, 1995) or as described in U.S. patent application Ser. No. 60/071,773, filed Jan. 19, 1998

Plant transformation vector pCGN8045 was transformed into strawberry plants using the following method:

Strawberry Micropropagation Transformation Protocol A

Plant Material

In vitro strains BHN FL90031-30 or BHN 92664-501 (CA-adapted) strawberry cultures are grown in presterilized Magenta GA7 boxes (Magenta Co., Chicago, Ill.) containing micropropagation medium (Table 3). Each unit of tissue contains two to three apical meristems, and two units are placed in each jar. The cultures are then incubated at about 22° C., with cool white light with 16/8 photoperiod at about 34–40 mEinsteins m-2 sec-1. About every four weeks, each unit of tissue is subdivided into two to four clumps and placed on fresh media of the same composition. Ideal stock material for explanting is available at two to three weeks after the last subculture.

TABLE 1

Selection medium A

| Component | Concentration |
| --- | --- |
| MS salts/MS vitamins (Sigma M0404) 4.4 g/L Glucose | 20 g/L |
| Washed Agar | 8 g/L |
| Thiodiazuron | 2.3 mg/L |
| Indoleacetic acid | 1.75 mg/L |
| Timentin | 500 mg/L |
| Cefotaxime | 100 mg/L |
| Kanamycin | 50 mg/L |
| pH adjusted to 5.7 | |

TABLE 2

Elongation medium A

| Component | Concentration |
| --- | --- |
| MS salts/MS vitamins (Sigma M0404) 4.4 g/L Glucose | 20 g/L |
| Washed agar | 8 g/L |
| Timentin | 500 mg/L |
| Cefotaxime | 100 mg/L |
| Indoleacetic acid | 0.45 mg/L |
| Galacturonic acid | 2.5 mg/L |

TABLE 2-continued

Elongation medium A

| Component | Concentration |
| --- | --- |
| Kanamycin | 50 mg/L |
| pH adjusted to 5.7 | |

TABLE 3

Micropropagation Medium

| Component | Concentration |
| --- | --- |
| MS salts (Sigma 0153) | 2.2 g/L |
| MS vitamins (Sigma M3900) | 1 mL/L |
| MgSO4.7H2O | 0.2797 g/L |
| CaCl2.2H2O | 0.2739 g/L |
| KH2PO4 | 0.5950 g/L |
| H3BO3 | 18.6 mg/L |
| NaMoO4.2H2O | 0.7 mg/L |
| Iron stock | 5 mL/L |
| Myo-inositiol | 100 mg/L |
| Ascorbic acid | 100 mg/L |
| N6-benzylaminopurine | 1 mg/L |
| Indolebutyric acid | 0.37 mg/L |
| Sucrose | 30 g/L |
| Washed agar | 8 g/L |
| pH adjusted to 5.8 | |

Agrobacterium Preparation

Four days prior to co-cultivation, Agrobacterium tumefaciens strain LBA4404 containing plant expression vectors were streaked from a frozen glycerol stock AB plate (AB media supplemented with 15 g Difco Bacto Agar, Table 4) containing 150 g/L streptomycin, 100 mg/L gentamicin and 100 mg/L kanamycin. Twenty-four hours prior to co-cultivation single colonies were placed into 5 mL of MG/L media (Table 5). Cultures were grown overnight at 30° C., 200 rpm agitation.

TABLE 4

AB media

| Component | Amount |
| --- | --- |
| 20X AB Stocks [120 g/L K2HPO4, 46 g/L NaH2PO4.H2O, NH4Cl, 6 g/L KCl] | 40 g/L 50 mL |
| 1 M MgSO4 | 1 mL |
| 0.1 M CaCl2 | 1 mL |
| 20% Glucose (w/v) | 25 mL |
| FeSO4.7H2O (0.25 mg/mL) | 10 mL |

TABLE 5

MG/L media

| Component | Concentration |
| --- | --- |
| Mannitol | 5 g/L |
| L-glutamic acid | 1 g/L |
| KH2PO4 | 0.25 g/L |
| NaCl | 0.10 g/L |
| MgSO4.7H2O | 0.10 g/L |
| Biotin | 1 mg/L |
| Tryptone | 5 g/L |
| Yeast extract | 2.5 g/L |
| pH adjusted to 7.0 | |

Explant Inoculation

Explanting and Pre-Culture Steps

Small folded leaves about 2–4 mm in length possessing a vibrant green, glassy appearance are excised at the petiole. They are placed into a petri dish containing about 1–1.5 mL of sterile water and a sterilized WHATMAN filter paper. The basal portion of the leaves is removed with a single cut such that 3 leaflets are produced from each leaf. The leaflets (explants) are placed onto the preculture plates (Table 6). The preculture plates are prepared using solid medium and pipetting 1 mL of TXD liquid medium which has been supplemented with 200 mM acetosyringone and 100 mM galacturonic acid onto the solid plate. Two sterilized WHATMAN filter papers are placed onto the plate. Approximately 50 explants are placed onto each preculture plate. The plates are placed under low light conditions for about three days by placing in an aluminum foil covered box.

TABLE 6

Preculture/co-culture medium with overlay

| Component | Concentration |
| --- | --- |
| MS salts/MS vitamins (Sigma M0404) 0.44 g/L Glucose | 30 g/L |
| Washed agar | 8 g/L |
| Thiadazuron | 2.2 mg/L |
| Indoleacetic acid | 1.75 mg/L |
| Acetosyringone | 39.28 mg/L |
| Galacturonic acid (100 mM) | 4 mL |
| pH adjusted to 5.7 | |

The overlay is 1 mL/plate of TXD liquid medium containing 200 mM acetosyringone, 100 mM galacturonic acid, and 2 sterile WHATMAN 8.5 cm filter papers.

Inoculation and Co-Culture Steps

The Agrobacterium suspension is diluted to $5 \times 10^8$ bacteria/mL with MG/L media just immediately prior to use. The explants are removed from the preculture plate and allowed to sit in 5 mL of bacterial suspension for 5 minutes. The explants are then removed from the bacterial suspension and blotted dry on sterile paper towels and placed back on the preculture plate. The explants are spread out uniformly adaxial side down so that all are in good contact with the filter paper and are not overlapping. These plates are then co-cultured under low light conditions for an additional 3 days.

Tissue Selection and Regeneration

The explants are moved to delay medium (Table 7) for 3 days, adaxial side down. The explants are stored under low light conditions during the delay period.

TABLE 7

Delay medium A

| Component | Concentration |
| --- | --- |
| MS salts/MS vitamins (Sigma M0404) 4.4 g/L Glucose | 20 g/L |
| Washed agar | 8 g/L |
| Thidiazuron | 2.3 mg/L |
| Indoleacetic acid | 1.75 mg/L |
| Timentin | 500 mg/L |
| Cefotaxime | 100 mg/L |
| pH adjusted to 5.7 | |

TABLE 8

Rooting Medium A

| Component | Concentration |
| --- | --- |
| MS salts (Sigma 0153) | 2.2 g/L |
| MS vitamins (Sigma M3900) 1 mL/L MgSO4.7H2O | 0.2797 g/L |
| Cacl2.2H2O | 0.2739 g/L |
| KH2PO4 | 0.5950 g/L |
| H3BO3 | 18.6 mg/L |
| NaMoO4.2H2O | 0.7 mg/L |
| Iron stock | 5 mL/L |
| Myo-inositiol | 100 mg/L |
| Ascorbic acid | 100 mg/L |
| Indolebutyric acid | 0.37 mg/L |
| Timentin | 500 mg/L |
| Cefotaxime | 100 mg/L |
| Glucose | 20 g/L |
| Washed agar | 8 g/L |
| pH adjusted to 5.7 | |

After the three day delay, the explants (about 50 per plate) are transferred adaxial side down onto selection medium A (Table 1) and are cultured for about 3 weeks in the light (20–40 mEinsteins m-2 sec-1). After about 3 weeks, the explants are placed on selection medium B (Table 9). Subcultures are performed every 3 weeks. By 6 weeks, transformed explants will produce green shoots and green callus. Only explants which contain this shooting material and green callus should be moved. If the explants associated with the shoots and green callus are still green and healthy, then the entire explant should be moved together with the regenerating material. By 9 to 12 weeks, green actively growing shoot units can be picked from the explants and placed by themselves on selection medium B (Table 9). Each actively dividing unit represents an independent event. Once the unit has tripled in size, individual shoots can be placed on elongation medium (Table 6). This step may take three to six weeks. Shoots are rooted on rooting medium (Table 8). This step requires approximately two to three weeks.

TABLE 9

Selection medium B

| Component | Concentration |
| --- | --- |
| MS salts/MS vitamins (Sigma M0404) 4.4 g/L Glucose | 30 g/L |
| Washed agar | 8 g/L |
| Thiadazuron | 3.4 mg/L |
| Indoleacetic acid | 0.45 mg/L |
| Timentin | 500 mg/L |
| Cefotaxime | 100 mg/L |
| Kanamycin | 50 mg/L |
| pH adjusted to 5.7 | |

Shoots are potted into 6-pack containers of Sunshine mix #1 (80% peat). The containers are placed into a misting tent on trays with dome lids for 3 days. Subsequently, the dome lids are tilted halfway to allow for airflow for 3 more days. The dome lid is removed after 6 days and plants stay under the misting tent for an additional 10 to 15 days. Plants are misted until they are taken out of the misting tent.

Plants are then taken out and set on a bench for 7 days and transplanted into 6 inch pots of 25% of each: peat, sand, pumice, and redwood mulch. Greenhouse day temperatures range from about 20–24.5° C. and the night temperatures are about 10–14.5° C. There is no artificial light, and light intensity is decreased from the end of May to the end of September by use of a shade cloth.

Example 4
Determination of Gene Expression

Plants transformed with promoter-GUS fusions may be examined for gene expression using methods well known in the art. Expression in response to exogenously applied auxin can also be examined using methods known in the art. The expression of the GUS enzyme would be expected to be similar to the expression of the SAR5 and RJ39 mRNAs.

One method involves GUS staining of plant tissue and examining the staining pattern. Plant tissue and fruit of plants transformed with promoter-GUS constructs may be harvested at different developmental stages and stained for β-glucoronidase activity. Fruit tissue may be sectioned and stained by infiltrating the tissue with GUS staining buffer (50 mM Potassium Phosphate (pH 7) 1 mg/ml X-Gluc (5-bromo-4-Chloro-3-indole-β-D-glucorinide) and 0.1% Trition X-100). Tissue is allowed to stain in the staining buffer overnight at 37°. The tissue is then destained using washes of 70% ethanol for 1 hour, then 100% ethanol. The tissue may then be examined visually for staining.

In order to quantify the expression, assays to determine the GUS enzyme activity may also be used (Jefferson, R. A., *Plant Mol. Biol.* Reporter (1987) 5:387–405). Total protein is extracted from plant tissue using GUS extraction buffer (50 mM Sodium Phosphate, pH 7.0, 10 mM β-mercaptoethanol, 10 mM EDTA, 0.1% Sodium Lauryl Sarcosine and 0.1% Triton X-100). Samples are centrifuged, and supernatant containing the protein is transferred to a new tube. Assays are carried out in Assay buffer (1 mM MUG (4-methyl umbelliferyl β-D-glucorinide in GUS extraction buffer). Fluorescence is measured using a fluorometer, and relative expression may be determined.

In addition, gene expression may be examined at the transcription level using Northern hybridizations. Total or poly(A)+ RNA may be isolated from fruit tissues, as well as other tissues, at different developmental stages. The RNA is then separated on a denaturing agarose gel and transfered to nylon membrane (Sambrook et. al., 1989). Hybridizations may then be performed using a labelled probe, and the hybridized membrane is then exposed to radiographic film. Expression of the mRNA transcript may be determined by observing the hybridization pattern of the membrane.

The above examples provide for the SAR5 and RJ39 promoters which may be used to provide for increasing or decreasing fruit receptacle tissue selective expression of heterologous genes during fruit development, maturation and ripening. Such a pattern of expression is particularly desirable for expression of genes for traits such as increased sugar content and disease resistance.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed:

1. A DNA construct comprising the promoter sequence from RJ39, isolated from Fragaria, operably-linked to a heterologous DNA coding sequence of interest.

2. The construct according to claim 1, wherein said promoter comprises the DNA sequence of SEQ ID NO:2.

3. The construct according to claim 1, comprising, in the 5'-3' direction of transcription said promoter, said DNA sequence of interest, and further comprising a transcriptional termination region functional in plants.

4. The construct according to claim 3, wherein said DNA sequence of interest is an open reading frame encoding an amino acid sequence.

5. The construct according to claim 3, wherein said DNA sequence of interest is complementary to mRNA endogenous to a plant cell.

6. The construct according to claim 1, wherein said DNA sequence of interest encodes a protein selected from the group consisting of sucrose phosphate synthase, ADP glucose pyrophosphorylase, invertase, glucose-6-phosphatase, and sucrose synthase.

7. The construct according to claim 1, wherein said DNA sequence of interest is a sequence which comprises a gene for resistance against a plant pathogen.

8. A method for modifying the fruit phenotype in a transgenic plant, said method comprising the steps of growing a transgenic plant to produce fruit tissue, wherein cells of said fruit tissue comprise in their genome one or more DNA constructs according to claim 1.

9. A transgenic plant produced by the method of claim 8.

10. A transgenic plant according to claim 9, wherein said plant is a strawberry plant.

* * * * *

SEQUENCE LISTING

<160> NUMBER OF SEQ ID NOS: 8

<210> SEQ ID NO 1
<211> LENGTH: 2061
<212> TYPE: DNA
<213> ORGANISM: Fragaria vesca
<220> FEATURE:
<221> NAME/KEY: promoter
<222> LOCATION: (1)..(2061)
<220> FEATURE:
<221> NAME/KEY: unsure
<222> LOCATION: (897)
<223> OTHER INFORMATION: position 897 can be represented by any nucleotide

<400> SEQUENCE: 1

```
ctcgagcact aaacaagtta agtaatctcc ctatctctgt tacaagcttg tattctttgg      60
ttgtgtacta accaatgtca ctgtcatatt gatccggctt aagatgttac tgatgcttat     120
gggcggtgaa ggtggatatt ccaaaggtaa ggttgttata caataccgaa gagtatacat     180
tctatgccta aactcccaat ttttttttt aattttttgg tgacgagaaa aaccattgtg     240
gttctttcct cccatcatgt atggtgtcct aatattggtg ttattcacct ggaaaaattc     300
gaaccaagaa acgtttgaac tagctgtgtt cttgactgga gagaatgaat caactacgga     360
ttttgagaaa caaatactat ccaacaaaga aaatgaggga gaaatgtcca tctgctaaaa     420
ttgttggcgt gaccgcaaca gagagtccac ggcccactga gaaccttgac gggcgaaggc     480
gcactgcaat atcaggggtg gggcccatct caatgcatgc aatgcctaag gcccatattt     540
cttttgatc ccacggccca gttcacttac cacgactact atatgttagt tttgttttta     600
tttcttatag gtttagctca cttagctgga agtcagtctc acgtttatta taggaataat     660
aaagttttgt atcgggaaaa actcaatata catgaagccc gagctacata actaggttct     720
aaaaatcggt ctgggcggcc gcctagacgc tcgacgatgg ctgcccgtct cgatttcaag     780
caaatcgtgt ggtctgggcg gctgtccgat tttcgattga ttactcggc tgggcggcga     840
ttactcaggc taggcggcga ttactcgggt tgggcgggtg ggcgggttgg cgggacnaga     900
ttctctcaac tggaaatcgt cttcgatatt gtccacgtcc atgagagata ggaacctttg     960
gagcctgagt tgaagacgat agagaagaag atgaaggaa cagaataagg agacgtgggt    1020
ttttagttct ttatgataat tgagatgagt tatctattac attaggctta atctaattgg    1080
gtctggaaag atattgactt tactgatggg tattcttta atagctttta cacaaattaa    1140
tccaataatt gttatccgtt tttctaagga caaggtttag gatatagttt attaggtgat    1200
taaaaattat ttaatattat attaaatgat tatttaagta ataattgct tgttataata    1260
attatatgca ttattatat aattatctat tattaaaaat aaaatattta acaaaaaata    1320
taaatccgat taatccccga ttaatctttt gggcgctatc cgcccgacta acgcctaaca    1380
ttttttaaaa ccttgtacct aagaaagcct ataacatcat gaatcaatat catgcaaaat    1440
cgtttaaaga aaacgtctga ttccaactct gtccatagga gttgaattca gaatccggag    1500
aatctgaatt taattctttc ttttattatt ttcgttcatt ctaaacgatg ttaaaaaaat    1560
ttaggacatg agacttaata tctagagcag tgtcacactt ataccaaagt agggaaccaa    1620
cgtgtcacta ttaatcacat gtctcccatc attctgggcc cttcttgctc tacggaatag    1680
gacaagtatt catatagtaa gggtacactt gtgaaccaag cctcgtctca ctaaatttct    1740
ctatgaatta tctttacata gcgggacccc agtttaccaa gtcttcatcc ttatccatgt    1800
```

```
tttcctcctt tttccactct ccaaattatc ctacaaccag tcgtagaatt aggaattacc    1860
accctgaggt tgaaactaaa gacacttgga agtagcagaa cggtgaagaa ccccattatc    1920
aaatcagtaa ctttctaata gtaaacccca agatatttt agctaccaag ctctcttata    1980
tatacaacca tccaggaaag acccagaaca cactaaaaag gaagagatcg agaaagaaag    2040
aaagagttca gagcaaagat g                                              2061

<210> SEQ ID NO 2
<211> LENGTH: 874
<212> TYPE: DNA
<213> ORGANISM: Fragaria vesca
<220> FEATURE:
<221> NAME/KEY: promoter
<222> LOCATION: (1)..(874)
<223> OTHER INFORMATION: RJ39C promoter

<400> SEQUENCE: 2
tctagacttg tatgcattac agcacgagca gttcatttca tgcatgacat gaaaacaacg      60
cgtggtgcaa tctactaaac cacgtgtacg gctaatctca ggggttttc tagggtttag     120 aatgtttcaa acatctatat taggttttgg agtttgcata gatacgttca aaagttaata    180
gcaaatttga aggtgtgcaa tgttaacatt gacctgttaa cttgtgattt ctagctgtaa    240
aacagataac gctttagcta atgctaagtt ttcacatttt catttcgggg ctaaatatat    300
ggttgtgagt aatgtttcag agatactttt aactttttga agatatagt ctcttaatgg     360 atatatatga gatgtaattt tatgagttat ctgtttcgat ttgaattcac gtttaggttt    420
aggattagct agcactttaa cattatcctg aaatatcttg gaaacaaatt tggtgttgtc    480
ctaacaataa tattattgtg ttgaaatttg cacattgcat ttttatgtgt tgaaatttta    540
tctaaaatgc ttggtggagc ataataattt gaaagagaa agagtcaata tgaatccgat     600
gcattcttgt cgtccagatt aactatttaa caaatatcca aatctatcta tatggttata    660
aattatattt attttctaaa tttacttcca tgtttttaat ttgccaggtc atcgatctaa    720
ttacacggta gagaatactc atgaaactgg aattctgaat attcacgtca gcacagatat    780
tagctggctc tgcttatctt tctctctatc caacactgtg attcaaaccc ccattaaatc    840
cagacctact gccacactgt ccctttcttc catg                                874

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: PCR primer
      SAR5-5C1
<220> FEATURE:
<221> NAME/KEY: primer_bind
<222> LOCATION: (1)..(27)

<400> SEQUENCE: 3
tcgaattcag agcaaagatg gttctgc                                         27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: PCR primer
      SAR5-3N2
<220> FEATURE:
<221> NAME/KEY: primer_bind
<222> LOCATION: Complement((1)..(27))
```

```
<223> OTHER INFORMATION: complementary to SAR5-5C1 sequence I.D. #3

<400> SEQUENCE: 4
acctcgaggg atcctcatca cttgtcg                                              27

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer
      pSAR5-BH1
<220> FEATURE:
<221> NAME/KEY: primer_bind
<222> LOCATION: (1)..(25)

<400> SEQUENCE: 5
taggatccgt ctttgctctg aactc                                                25

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer
      PSAR5-R4
<220> FEATURE:
<221> NAME/KEY: primer_bind
<222> LOCATION: (1)..(20)

<400> SEQUENCE: 6
accttgtacc taagaaagcc                                                      20

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Primer
      RJ39C-3N1
<220> FEATURE:
<221> NAME/KEY: primer_bind
<222> LOCATION: (1)..(30)

<400> SEQUENCE: 7
aactgcagat ctagtgtggc agtaggtctg                                           30

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: T7 Promoter
      Primer
<220> FEATURE:
<221> NAME/KEY: primer_bind
<222> LOCATION: (1)..(20)

<400> SEQUENCE: 8
taatacgact cactataggg                                                      20
```